United States Patent [19]
Cerofolini

[11] Patent Number: 5,740,804
[45] Date of Patent: Apr. 21, 1998

[54] MULTIPANORAMIC ULTRASONIC PROBE

[75] Inventor: Marino Cerofolini, Subbiano, Italy

[73] Assignee: Esaote, S.p.A., Casale Monferrato, Italy

[21] Appl. No.: 733,499

[22] Filed: Oct. 18, 1996

[51] Int. Cl.[6] .............................. A61B 8/00; G01B 15/00
[52] U.S. Cl. .................. 128/660.1; 128/662.06; 73/633
[58] Field of Search ................. 128/662.06, 662.03, 128/660.08, 660.09, 660.01; 73/633

[56] References Cited

U.S. PATENT DOCUMENTS

| | | |
|---|---|---|
| 4,543,960 | 10/1985 | Harui . |
| 4,802,487 | 2/1989 | Martin et al. ............... 128/662.06 |
| 4,869,258 | 9/1989 | Hetz . |
| 4,932,414 | 6/1990 | Coleman . |
| 4,977,898 | 12/1990 | Schwarzschild . |
| 5,085,221 | 2/1992 | Ingebrigtsen . |
| 5,255,681 | 10/1993 | Ishimura . |
| 5,255,684 | 10/1993 | Rello .............................. 128/662.06 |
| 5,445,154 | 8/1995 | Larson . |

*Primary Examiner*—Francis Jaworski
*Attorney, Agent, or Firm*—Baker & Daniels

[57] ABSTRACT

A ultrasonic probe for use in transthoracic echocardiography to produce panoramic images of the area of interest and comprising a transducer array connected to a first and second rotating mechanism, wherein the rotating mechanisms are driven using open loop control signals. The first and second rotating mechanisms comprise first and second stepper motors to accurately rotate the transducer array through a particular scan plane and adjust the scan plane. Microstepping techniques are utilized to permit greater accuracy and control. Further, the first and second rotating mechanism comprise gear assemblies which permit the transducers to rotate through a wide angle to generate panoramic ultrasound images.

28 Claims, 6 Drawing Sheets

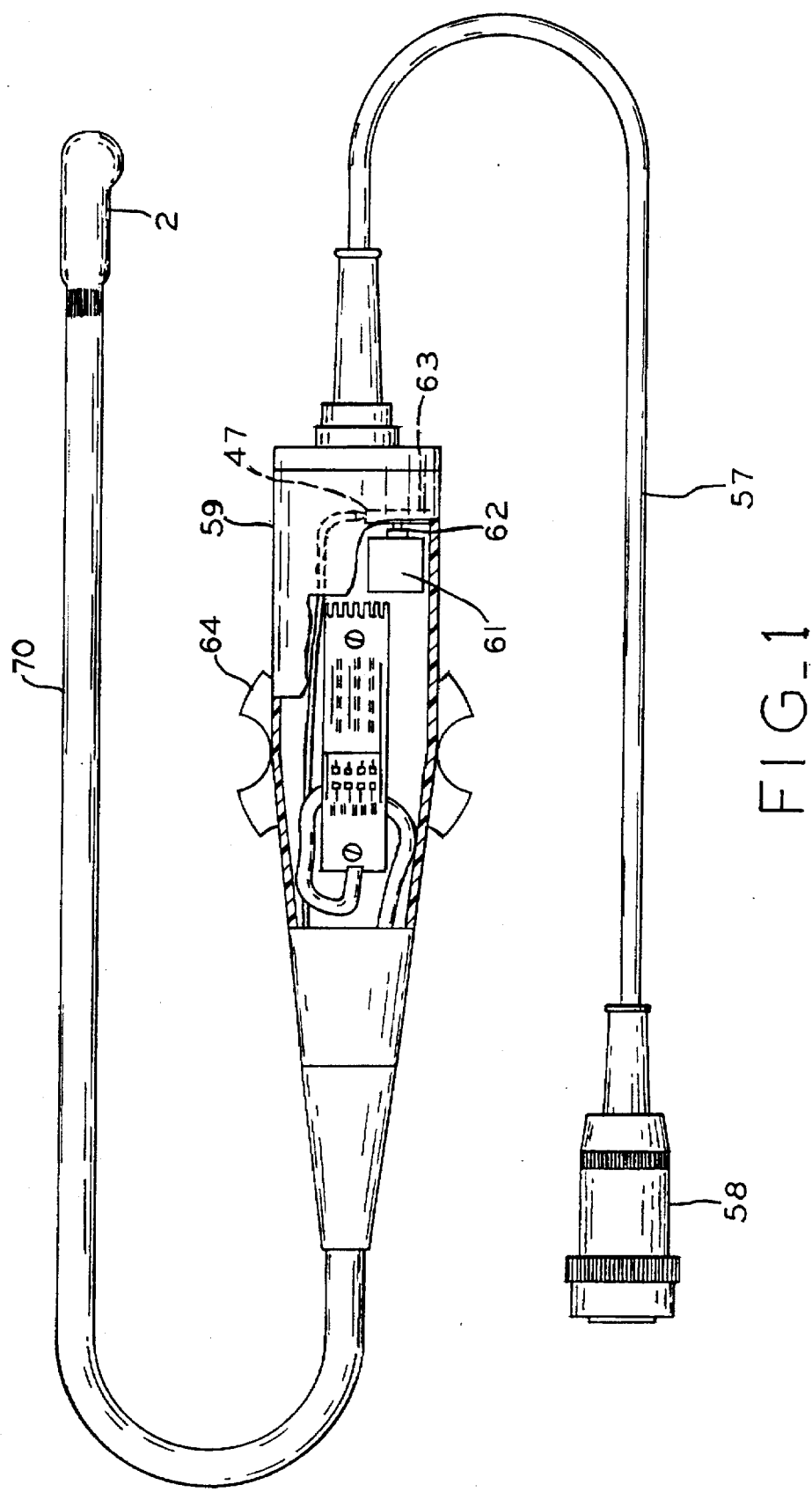
FIG_1

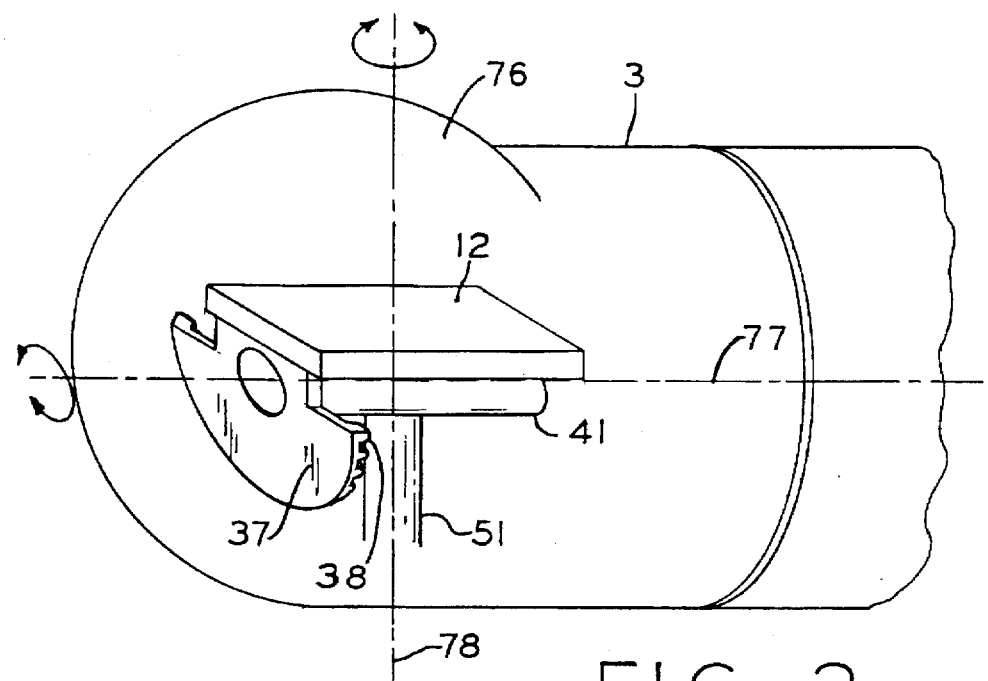
FIG_2
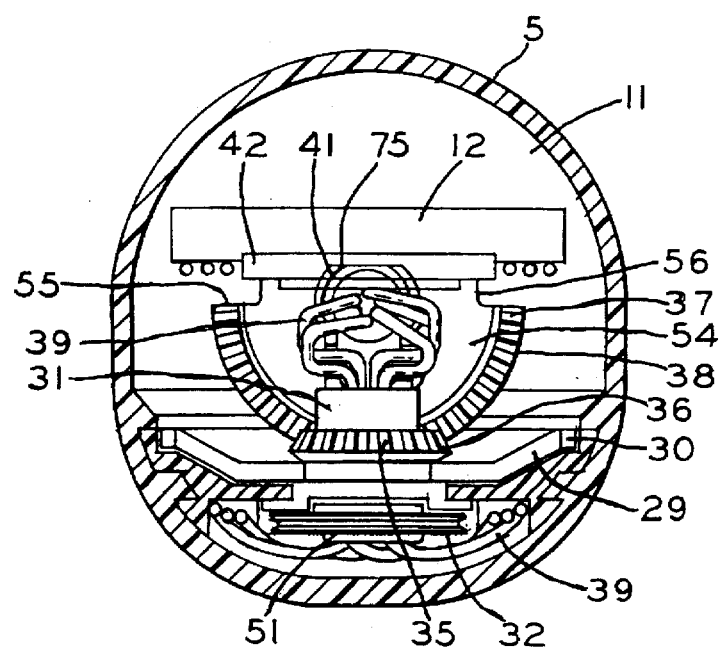
FIG_6

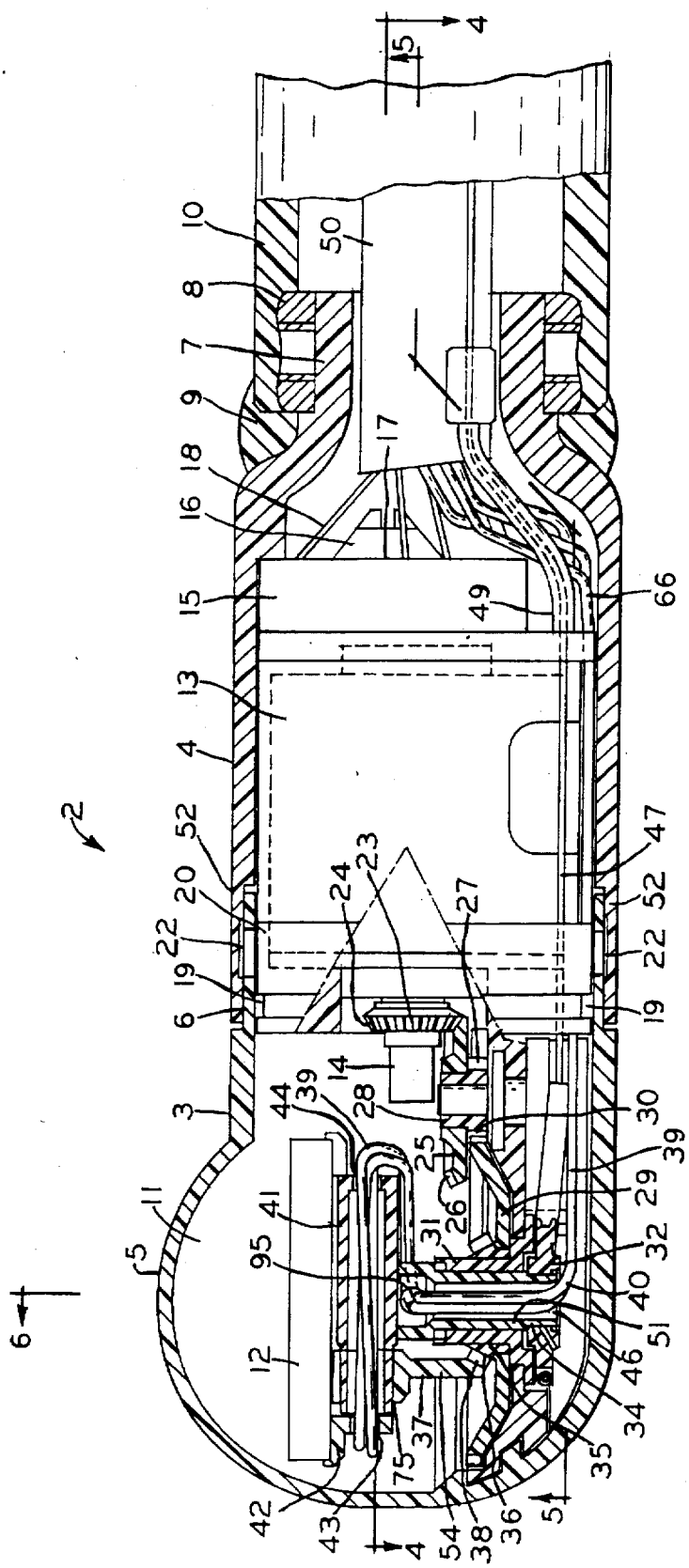
FIG._3

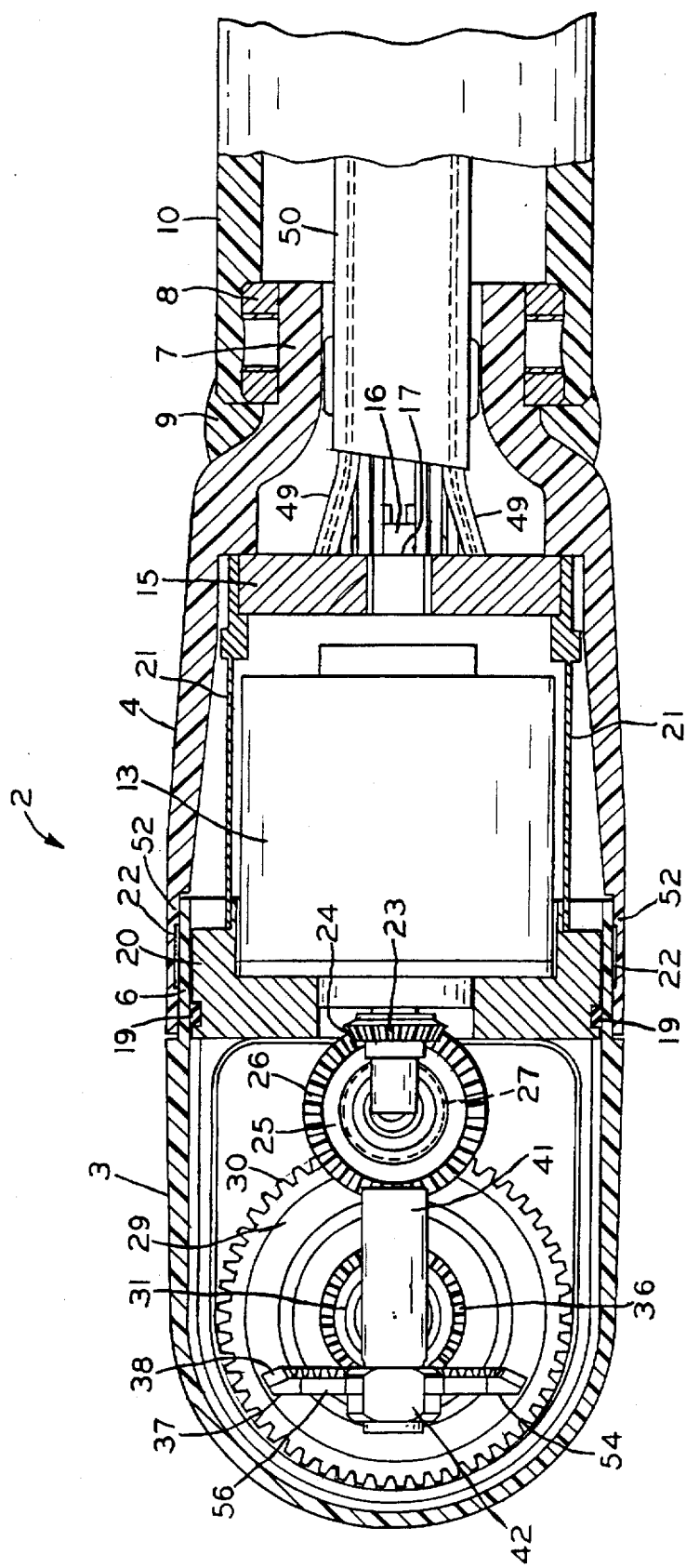
FIG._4

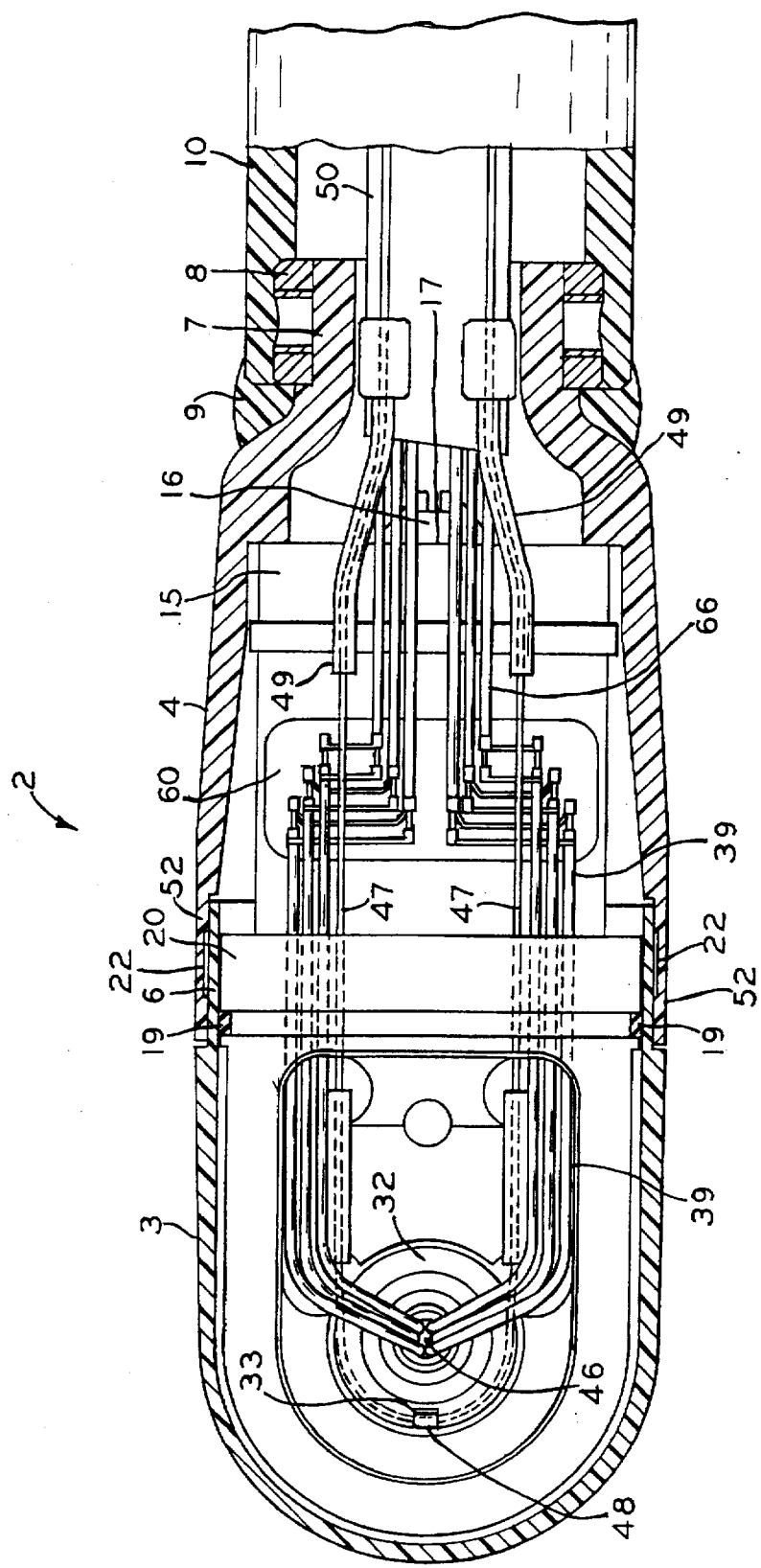

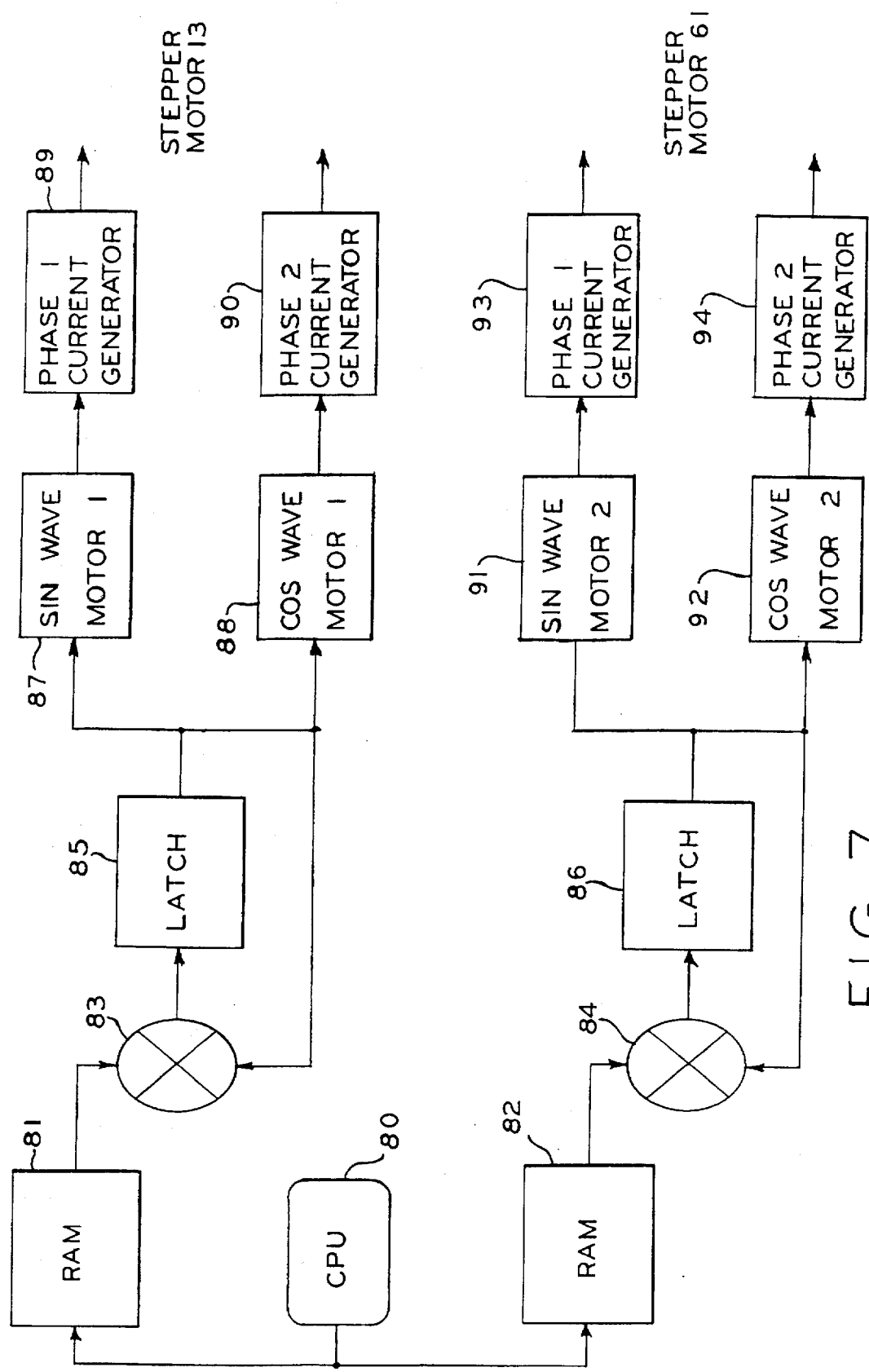
FIG._7

MULTIPANORAMIC ULTRASONIC PROBE

BACKGROUND OF THE INVENTION

1. Field of the Invention

The present invention relates to ultrasonic imaging systems and in particular to an ultrasonic probe assembly having a compact probe head design containing a transducer array which, while scanning a real time two dimensional image, is accurately rotatable through two mutually perpendicular axes.

2. Description of the Related Art

Ultrasonic imaging is a widely used method for obtaining an image of a patient's internal organs in real time due to its relative simplicity and non-invasive nature. In ultrasonic imaging, acoustic waves are generated by a transducer and directed toward an area of interest. The resulting echo is detected by the transducer array and analyzed by an imaging system to develop a real time image of the organs in the area of interest.

Transthoracic echocardiography (TTE) is a widely used procedure that uses ultrasonic imaging techniques to generate an image of a working heart.

One problem associated with TTE is interference and attenuation of the acoustic signal by intervening material disposed between the probe and the heart. For example, air pockets, bones, lung, etc. may all distort the original acoustic signal and the return echo thereby producing a poor echocardiographic image. A solution to this problem is to position the acoustic probe as close to the heart as possible, namely in the esophagus at the level of the heart. By placing the transducer array close to the heart, much of the interference and attenuation associated with intervening materials can be eliminated. However, in order to maneuver and position the transducer as close to the heart as possible, the probe must be sufficiently compact and controllable. Therefore, space considerations are very important in designing a TTE probe.

The reduction in the size of TTE probes has been limited by the functional requirements of the transducer array housed in the TTE probe. In order to optimally produce an effective series of real time images capable of representing the heart in two dimensions, the TTE probe must be capable of directing and receiving acoustic signals about two separate axes. Essentially, the transducer array must be capable of scanning through a particular scan plane as well as through a plurality of scanning planes. Moreover, in order to represent in one scan section the heart basal structures (atria, pulmonic vessels, aorta, etc.), the probe must be able to produce the highest possible scan angle. However, this angle has been limited to less than 100° in currently existing probes with multiplane capabilities.

Two different types of scanners have been used to implement such scanning, namely electronic sector scanners and mechanical sector scanners. In an electronic sector scanner, also known as a phased array probe, the probe comprises a transducer array which is made of a plurality of transducer elements and capable of electronically steering the acoustic wave to produce a sector scan. The transducer array is also mechanically rotated to obtain the different scan planes. However, electronic sector scanners are very costly and the transducer arrays are physically limited to a sector scan of about 90°.

In a mechanical sector scanner, a mechanical drive device physically rotates a transducer array through the desired scan sector. The mechanical drive mechanism usually comprises a drive motor coupled to the transducer array through a mechanical linkage comprising, for example, cables, gears and/or pulley assemblies. A number of separate drive mechanisms may be required, with each drive mechanism having an associated mechanical linkage for rotating the transducer array through a particular scan plane and through a plurality of scan planes. Due to space considerations, the drive motor is usually placed in an external housing and a length of cable running from the external housing to the probe head couples the drive motor to the transducer array.

Although the cost of mechanical sector scanners is lower than electronic sector scanners, mechanical sector scanners have not found widespread clinical use due to a number of problems. One problem with mechanical scanners is that an indirect mechanical linkage inherently generates errors due to errors associated with the engagement of various mechanical elements. The cables and linkage assemblies may be disposed over a relatively large length, making accurate control of the transducer array difficult. The inevitable stretching, twisting and distortion of the cables and linkage assembly can create inaccuracy in the control of the transducer array position.

Further, if the associated imaging and control systems use the movement of the drive motor to determine the position of the transducer array and generate an image based on such position information, the resulting image will be distorted and even unusable. If the associated imaging and control system uses a position indicating mechanism, such a mechanism must be placed in the probe housing near the transducer array, thus increasing the size of the probe.

One attempt to avoid the problems noted above has been to directly couple the transducer array to the shaft of a drive motor disposed in the probe, thereby enabling the drive motor to directly rotate the transducer array. However, a position sensing device is still needed near the transducer array to ensure sufficiently accurate determination of the array position. Also, directly coupling the transducer array to a drive motor shaft only allows the transducer array to rotate about a single axis, thus allowing the scanning of a particular scan plane but not allowing rotation through different scan planes. Adjustment of the scan plane requires the probe housing to be physically rotated, which limits the effectiveness of this design.

Another attempted solution places two separate transducer arrays in the probe with both probes driven by a single drive motor. The transducer arrays are disposed at predetermined angles with respect to each other such that one array scans a particular scan plane while the second array scans an envelope of a cone centered about the axis of the probe housing. However, this solution also is not entirely satisfactory. This arrangement increases the cost and size of the probe housing since two transducer arrays, as well as a mechanical linkage for each transducer array, are required. Further, rotation of the transducer array through a plurality of scan planes is not possible since the second transducer array is affixed at a predetermined angle with respect to the probe housing axis. Furthermore, current multiplane mechanical devices have not overcome the sector size limitations, typical of the phased arrays.

Thus, an objective of this invention is to provide a compact ultrasonic probe having a transducer array enclosed therein which a single transducer array is capable of wide scanning through a given scan plane and rotating through a plurality of scan planes to generate a panoramic echocardiographic image.

Another objective of this invention is to provide a compact ultrasonic probe assembly having drive mechanisms which utilize open loop control techniques to control the rotation of the transducer array. Thus, the position of the transducer array is determined by open loop commands applied to the drive mechanisms, thereby obviating the need for a position sensor in the probe housing.

Another objective of this invention is to provide a compact ultrasonic probe assembly having a transducer array which is rotatably positioned using a microprocessor based control device wherein the transducer array moves through a predetermined angle in response to a pulsed signal generated by the microprocessor.

Another objective of this invention is to provide a compact ultrasonic probe assembly having the transducer array, motor and gear-only assembly all within probe housing for its scan rotation. It has the advantages of slippage-free and utilization of much smaller motor in both physical size mad power requirement due to the gear-only assembly and the close proximity between the transducer array and the motor.

SUMMARY OF THE INVENTION

An ultrasonic probe according to the present invention includes a transducer array connected to first and second rotating mechanisms which rotate the transducer array about two mutually perpendicular axes. The first and second rotating mechanisms rotate the transducer array through a wide angle about both axes to produce a panoramic image along the area of interest of multiple scan planes. The first and second rotating mechanisms utilize open loop control techniques to rotate the transducer array through a predetermined angle in response to first and second open loop signals, respectively. Since the rotating mechanisms act in response to open loop signals, feedback and position detection mechanisms are not required.

In an exemplary embodiment, the ultrasonic probe includes first and second rotating mechanisms, comprising first and second stepper motors, respectively, operatively connected to a transducer array. The first stepper motor is disposed in the probe housing and rotates the transducer array through a particular scan plane. The second stepper motor is disposed in the second housing and rotates the transducer array through a plurality of scan planes. The wiring and control cables associated with the transducer array and the rotating mechanisms are carried within a flexible connection disposed between a probe housing and the second housing. Microstepping techniques are applied to the first and second stepper motors to more finely control the rotation of the first and second stepper motors.

In another exemplary embodiment, an ultrasonic imaging system is disclosed. The ultrasonic imaging system comprises the ultrasonic probe assembly described above operatively connected to a control system comprising a microprocessing device which generates the first and second open loop signals, receives the echo information, and processes the information to produce an ultrasonic image. This system uses digital techniques to rotate the transducer array and process the echo information.

The construction and operation of stepper motors is well known in the art. Such construction and operation are described in, for example, *Industrial Electronics*, James T. Humphties and Leslie P. Sheets, Delmar Publishers Inc., 1993, pages 154–165, and *Modern Industrial Electronics*, Charles A. Schuler and William L. McNamee, MacMillan/McGraw-Hill, 1986, pages 52–58.

The use of stepper motors in an ultrasonic probe is uniquely advantageous for a number of reasons. As is well known in the art, a stepper motor is an electromagnetic device which converts electric pulses into discrete mechanical motion. A stepper motor is constructed with a number of natural detent positions on the rotor and the stator. The rotor rotates to change the alignment of the detent positions as the windings are energized and deenergized by the electric pulses. Extremely fine control of the rotor position can be obtained by increasing the number of detent positions on the rotor.

Stepper motors can also be construed to be extremely compact, making them suitable for placement within an ultrasonic probe housing. For example, stepper motors may be sized to have a volume of a few cubic millimeters.

An advantage associated with using stepper motors in an ultrasonic probe is that stepper motors use an open loop control system based on open loop commands. Unlike servos, or other similar devices which utilize feedback or closed loop controls, the rotation of a stepper motor to a desired angle is determined entirely by an open loop command. Since the rotation of a stepper motor is directly controlled by the number of pulses applied to the motor windings, a stepper motor can be designed and constructed for very accurate position control, thereby obviating the need for position detection devices. The position of a stepper motor can be accurately determined by a control system which generates the control signals and stores information about these control signals. Such a control system can easily be implemented utilizing digital technique to increase accuracy by using, for example, a microprocessor. This feature increases the accuracy of the ultrasonic imaging system and reduces the space requirement for the drive mechanism and the scanning head as a whole.

Another advantage of a stepper motor based system is that the system is extremely stable and is not subject to drift errors because such a system is digitally controlled using open loop commands. The velocity of the rotor is proportional to the frequency of the drive signal and the position of the rotor is determined by the number of pulses sent by the control system. Therefore, any drift errors that may be present are not cumulative and the movement of the rotor is highly accurate and repeatable.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 1 is a plan view of the probe of the present invention including a partial cut away view of the hand held control portion;

FIG. 2 is a perspective view of the probe scanhead showing the face of the scanhead and the two perpendicular axes of rotation;

FIG. 3 is an elevational cross sectional view of the probe scanhead of the present invention;

FIG. 4 is a cross sectional view of the probe scanhead of the present invention taken along the line A—A of FIG. 3;

FIG. 5 is a cross sectional view of the probe scanhead of the present invention taken along the line B—B of FIG. 3;

FIG. 6 is a cross sectional view of the probe scanhead of the present invention taken along the line C—C of FIG. 3; and FIG. 7 is a block diagram of the portion of the control system for generating and applying the scan plane selecting and scanning signal.

Corresponding reference characters indicate corresponding parts throughout the several views. Although the drawings represent an embodiment of the present invention, the drawings are not necessarily to scale and certain features may be exaggerated in order to better illustrate and explain the present invention. The exemplification set out herein illustrates an embodiment of the invention, and such exemplification is not to be construed as limiting the scope of the invention in any manner.

DETAILED DESCRIPTION OF THE INVENTION

The embodiments disclosed below are not intended to be exhaustive or limit the invention to the precise forms disclosed in the following detailed description. Rather, the embodiments are chosen and described so that others skilled in the art may utilize their teachings.

Referring to FIGS. 1–3, ultrasonic probe assembly 1 of the present invention comprises scanhead 2, which houses transducer array 12 and its associated rotating assemblies. Transducer array 12 transmits and receive acoustic information through face 76 of scanhead 2. Transducer array 12 is mounted on a first and a second rotating assembly which rotate transducer array 12 about two separate, mutually perpendicular, axes 77 and 78. Rotation about first axis 77 constitutes scanning rotation in a particular scan plane and rotation about second axis 78 constitutes scan plane adjustment rotation. First axis 77 lies parallel to the lengthwise direction of transducer array 12. Second axis 78 is perpendicular to first axis 77. As transducer array 12 rotates about second axis 78, first axis 77 also rotates about second axis 78 to maintain its parallel relationship with transducer array 12. The first and second rotating assemblies comprise scanning stepper motor 13 and scan plane adjusting stepper motor 61, respectively, connected to transducer array 12 through various gear assemblies, as described below.

Referring further to FIGS. 3–5, scanhead 2 comprises generally cylindrical probe head housing 3 attached to cylindrical tubular rear housing 4. Head housing 3 includes bulbous portion 5 integrally connected to a cylindrical tubular portion having fitting portion 6 disposed on the open end. Rear housing 4 includes narrow diameter end portion 7 at one end and fitting portion 52 at the other end. Fitting portion 6 of head housing 3 sealingly engages fitting portion 52 of the front end of rear housing 4 to form a single housing. The connection between head housing 3 and rear housing 4 is tightly sealed by housing seal 22. Head housing 3 and rear housing 4 are made of appropriate plastic material which are well known in the art to be transparent to acoustic waves for optimal acoustic transmission.

Bulbous portion 5 surrounds chamber 11 which houses transducer array 12 and various elements associated with the first and second rotating assemblies. Acoustic waves are transmitted and echo information are received by transducer array 12 through bulbous portion 5. Chamber 11 is sized to permit free rotation of transducer array 12 through as wide a scanning range and scan plane adjustment range as possible. Chamber 11 is also filled with appropriate liquid which are known in the art to be optimal for acoustic transmission. Such liquids are well known in the art and include, Polyethyleneglycol, sunflower oil or almond oil.

The construction and composition of transducer arrays are well known in the art and any such known transducer array may be used in the present invention.

The structure and operation of the first rotating assembly for mounting and rotating transducer array 12 about first axis 77 will now be described with references to FIGS. 3–6. The first rotating assembly comprises scanning stepper motor 13 which is connected to and rotationally drives transducer array 12 by means of a scanning gear assembly. Details of the operation of scanning stepper motor 13 are provided further below.

As shown in FIGS. 3–5, scanning stepper motor 13 is disposed inside rear housing 4 and enclosed by motor housing 20. Motor housing 20 fittingly engages scanning stepper motor 13 and rear probe housing 4 to prevent the movement of scanning stepper motor 13 within rear housing 4. Drive control signals are provided to scanning stepper motor 13 by stepper motor wires 18 which are disposed inside wire cover 50 and routed through probe shaft 10. Scanning stepper motor 13 is separated from chamber 11 by the front wall of motor housing 20.

Oil filling aperture 17 is provided at the rear wall of motor housing 20 to allow the filling of Chamber 11 with the appropriate liquid. Closing screw 16 is provided to seal oil filling aperture 17 when aperture 17 is not used.

The scanning gear assembly for rotating transducer array 12 about a given scan plane comprises a plurality of interconnected bevel gears and planar gears to transmit the rotation of scanning stepper motor 13 to transducer array 12. As shown in FIGS. 3 and 4, motor shaft 14 of scanning stepper motor 13 extends through the front wall of motor housing 20 to engage bevel gear 23. Bevel gear 23 engages bevel gear 25 by the engagement of gear teeth 24 and gear teeth 26. Bevel gear 25 in turn includes gear teeth 27 which engage gear teeth 30 of planar gear 29. Planar gear 29 rotates about base support 31 which is fixed relative to scanhead 2. Planar gear 29 engages scanning bevel gear 37 by the engagement of beveled gear teeth 36 and 38. Bevel gear 37 includes aperture 75 which fittingly engages the outer surface of tubular portion 41 such that bevel gear 37 rotates about tubular portion 41. Based on the arrangement described above, motor shaft 14 rotates scanning bevel gear 37, via bevel gear 23, bevel gear 25 and planar gear 29, about the axis of tubular portion 41.

As shown in FIGS. 3 and 6, bevel gear 37 is semi circular frusto-conical in shape and includes flat portion 54 and straight edge portion 55. Attachment base 42 is affixed to raised portion 56 disposed on straight edge portion 55. Transducer array 12 is fixedly attached to attachment base 42 for rotational movement with bevel gear 37. The above described arrangement allows the transducer array to rotate through a scanning angle of 180° about first axis 77.

The operation of the first rotating mechanism is now described. Based on a control signal provided by the control system to scanning stepper motor 13, motor shaft 14 rotates through a predetermined angle. The rotation of motor shaft 14 rotates bevel gear 23, thereby rotating bevel gear 25 by a proportional angle about shaft 28. Due to the engagement of gear teeth 27 and gear teeth 30, bevel gear 25 rotates planar gear 29 by a proportional amount. Further, due to the engagement of beveled gear teeth 36 and gear teeth 38, planar gear 29 rotates scanning bevel gear 37 by a proportional amount. Therefore, the rotation of shaft 14 is translated into the rotation of transducer array 12 about an axis which is parallel to tubular portion 41 and centered on the axis of scanning bevel gear 37. Flexible wire portions 40 allow transducer array 12 to move freely.

Referring to FIGS. 1 and 5, the second rotating means comprises scan plane adjusting stepper motor 61 disposed within second housing 59. Stepper motor 61 is connected to transducer array 12 by a scan plane adjusting gear assembly including cable 47. Motor shaft 62 of scan plane stepper motor 61 is connected to scan plane adjust pulley 63 on which cable 47 rides. As shown in the cutaway portion of FIG. 1, cable 47 extends through second housing 59, probe shaft 70 and into scanhead 2. As further shown in FIGS. 3 and 5, cable 47 extends through rear housing 4 about the periphery of motor housing 20 and into head housing 3 to engage pulley 32. Depression 33 on pulley 32 engages bulb 48 attached to cable 47 to prevent slippage between cable 47 and pulley 32 thereby ensuring accurate control of pulley 32 rotation. Pulley 32 is attached to inner shaft 51 which rotates and is disposed about fixed base support 31. Inner shaft 51 is fixedly attached to tubular portion 41 such that the rotation of inner shaft 51 also rotates transducer array 12 via tubular portion 41. The second rotating means of the present invention permits the transducer array to rotate through a scan plane range of 180° about second axis 78.

The operation of the second rotating means is now described. An appropriate electrical signal by a control system rotates motor shaft 62 of scan plane adjusting stepper motor 61 through a predetermined angle. The rotation of motor shaft 62 is transmitted to a scan plane adjust pulley 32 by means of cable 47. The movement of cable 47 and bulb 48 rotates pulley 32 about an axis defined by inner shaft 51 by an angle proportional to the rotation of motor shaft 62. The rotation of pulley 32 rotates inner shaft 51 which rotates transducer array 12 about axis 78 thereby adjusting the scan plane.

Further, as shown in FIGS. 3, 4 and 6, tubular portion 41 is attached adjacent to transducer array 12 and parallel to the center line of transducer array 12. Tubular portion 41 serves as a conduit for transducer wiring 39. Transducer wiring 39 is routed in an orderly manner through scanhead 2 through tubular portion 41, inner shaft 51, and along the periphery of head housing 3 into rear housing 4. Flexible portions 40 provided along the length of transducer wiring 39 near the vicinity of openings to tubular portion 41 and inner shaft 51 allow transducer array 12 to turn freely.

As indicated in FIG. 5, transducer wiring 39 extends along the periphery of motor housing 20 into rear housing 4. The ends of transducer wiring 39 are then attached to a printed connection board 60. Corresponding transducer wiring 66 is connected to the respective transducer wiring 39 at printed connection board 60 and extends out through the rear opening of scanning head 2 and is routed through probe shaft 10. Transducer wiring 66 may be connected to further control systems as necessary. Transducer wiring 39 and 66 transmit the required signals to actuate transducer array 12 and return the echo information to the control system as necessary to generate and display an ultrasonic image. Such images may then be displayed, for example on a CRT. Connecting transducer wiring 39 and transducer wiring 66 using printed connection board 60 simplifies the assembly process by allowing independent assembly of various portions of scanhead 2. Such a connection also simplifies scanhead replacement and servicing by allowing sectional replacement of scanhead 2.

The structure and operation of the stepper motors used in the present invention are now described. The ultrasonic probe of the present invention utilizes stepper motors to rotate transducer array 12 about two axes. The first and second rotating means comprise scanning stepper motor 13 and scan plane adjusting stepper motor 61, respectively. Scanning stepper motor 13 is housed in rear housing 4 and rotates transducer array 12 in a given scan plane. Scan plane adjusting stepper motor 61 is housed in second housing 59 and rotates transducer array 12 through a plurality of scan planes.

The construction and operation of stepper motors, and the advantageous of using such motors in an ultrasonic probe assembly, have been discussed above. The stepper motors and the control system of the present invention utilizes microstepping techniques to further ensure smooth rotation and extremely accurate position control of the transducer array. Microstepping techniques are well known in the art and involve the application of sinusoidal currents to the stator windings, rather than discrete pulses, to move the rotor smoothly without jerking. Microstepping allows extremely accurate and smooth control of rotor movement and is particularly suited for Issuer applications. By slowly changing the current through the rotor windings, rather than applying abrupt "on" and "off" transitions, a smooth torque is induced on the rotor to prevent the rotor from stopping or oscillating. The frequency of the current determines the angular velocity of the rotor and can easily be adjusted as necessary. The phase current may also be held at an intermediate value to keep the rotor at a particular angle.

Microstepping is also advantageous because microstepping can be implemented with a large number of microsteps to produce high positional resolution. Each pulse sent by the control system moves the rotor one microstep and the number of microsteps per step can easily be programmed into the control system. Thus, the control system can be designed to move the rotor over a very small angle for each pulse allowing extremely fine control of the rotor position.

A number of commercially available stepper motors which are sufficiently compact, or can be modified to be sufficiently compact may be utilized in the present invention. Control systems used with stepper motors, particularly those that utilize a microprocessor to generate control signals and determine angular position based on these control signals, are well known in the art. Such control systems may be easily reprogrammed or reconfigured as necessary based on the operating and design characteristics of the particular stepper motor used in the ultrasonic probe assembly. These operating and design characteristics are readily available from the manufacturer. For example, the present invention utilizes an EPSON STP10NI 20S stepper motor, which incorporates the following characteristics:

| Angle of Rotation per Step | 18 |
| --- | --- |
| Number of Phases | 4 |
| Drive System | Bipolar |
| Motor Drive Voltage | 5 V |
| Winding Resistance | 20 ohms |
| Detect Torque | 3 gm · cm |
| Holding Torque | 23 gm · cm |
| Rotor Inertia | 0.03 gm · cm$^2$ |
| Weight | 5 gm |

The pulse rate-torque characteristic of this stepper motor is optimal for most transesophageal echocardiography applications. A typical ultrasonic cardiac imaging system scans through a 90° scan angle with 100 acoustical lines at 18 images per second, which translates to 1,800 acoustical lines per second. Using the EPSON STP10NI 20S stepper motor a good correlation between the acoustical scan line rate and each physical step can be achieved (up to 1:1), resulting in very precise position control and good torque characteristics.

FIG. 7 illustrates the block diagram of a portion of the control system of an embodiment of the present invention comprising a control device for coordinating the operation of a ultrasonic imaging system. The control device comprises a microprocessing device for generating and applying drive signals to the stepper motors and using the drive signals to derive positional information. As discussed above, the present invention utilizes microstepping techniques which apply sinusoidal currents to the stator windings to produce smooth rotor motion and high positional resolution. The control system comprises CPU 80 which coordinates and controls the activities of various elements of the ultrasonic imaging system, including generating first and second control signals to scanning stepper motor 13 and scan plane adjusting stepper motor 61, respectively. Each stepper motor includes two windings, wherein a phase 1 current and a phase 2 current is applied to each winding, respectively.

The control signals generated by CPU 80 are initially loaded into RAM 81 and RAM 82, where they are read by incremental adders 83 and 84, respectively. The desired digital position information is then read from latches 85 and 86 respectively and converted to analog sine and cosine waves as necessary by converters 87, 88, 91, 92 and applied to the respective windings of the respective stepper motors through blocks 89, 90 and 93, 94 which generate a current proportional to voltage to prevent overheating in case of a short circuit. Thus, the pulses generated by CPU 80 are converted to sinusoidal signals for driving stepper motors 13 and 61.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

I claim:

1. An ultrasonic probe, comprising:
   an ultrasonic transducer array having a gear;
   control means for generating a first and a second open loop electrical control signal;
   first rotating means having an output shaft with a bevel gear engaging said gear of said ultrasonic transducer array for rotating said ultrasonic transducer array about a first axis through a predetermined angle, said first rotating means coupled to said control means to rotate said transducer array in response to said first open loop electrical control signal; and
   second rotating means connected to said ultrasonic transducer array for rotating said transducer array about a second axis through a predetermined angle, said second rotating means coupled to said control means to rotate said transducer array in response to said second open loop electrical control signal, said second axis perpendicular to said first axis.

2. The ultrasonic probe in accordance with claim 1, further comprising a probe housing, said transducer array and said first rotating means disposed within said probe housing.

3. The ultrasonic probe in accordance with claim 1, wherein said first rotating means comprises a first stepper motor.

4. The ultrasonic probe in accordance with claim 3, wherein said first stepper motor is operatively connected to said bevel gear, whereby the rotation of said first stepper motor through a predetermined angle causes said bevel gear and said transducer array to rotate about said first axis by a predetermined proportional amount.

5. The ultrasonic probe in accordance with claim 1, wherein said second rotating means comprises a second stepper motor.

6. The ultrasonic probe in accordance with claim 1, wherein said second stepper motor further comprises a pulley connected to said transducer array, said pulley operatively connected to said second stepper motor by a cable, said pulley having a depression on the rim and said cable having a bulb engaging said depression, whereby the rotation of said second stepper motor through a predetermined angle causes said pulley and said transducer array to rotate about said second axis by a predetermined proportional amount.

7. The ultrasonic probe in accordance with claim 1, wherein said bevel gear and said transducer gear are disposed within said probe housing.

8. The ultrasonic probe in accordance with claim 1, wherein said control means includes pulse generating means for generating said first and second open loop electrical control signals as respective first and second pulse trains.

9. The ultrasonic probe in accordance with claim 8, wherein said pulse generating means includes microstepping pulse means for generating analog signals in combination with said first and second pulse trains.

10. The ultrasonic probe in accordance with claim 9, wherein said pulse generating means generates sinusoidal signals.

11. An ultrasonic probe assembly, comprising:
    a probe housing;
    an ultrasonic transducer array disposed in said probe housing, said transducer array including a gear;
    control means for generating a first and a second open loop electrical control signal;
    first rotating means having an output shaft with a bevel gear engaging said gear of said ultrasonic transducer array for rotating said ultrasonic transducer array about a first axis through a predetermined angle, said first rotating means coupled to said control means to rotate said transducer array in response to said first open loop electrical control signal;
    second rotating means connected to said ultrasonic transducer array for rotating said transducer array about a second axis through a predetermined angle, said second rotating means coupled to said control means to rotate said transducer array in response to said second open loop electrical signal, said second axis to perpendicular said first axis;
    said first motor means disposed within said probe housing;
    said bevel gear and said transducer gear disposed within said probe housing; and
    a second housing connected to said probe housing by a flexible tubular connector.

12. An ultrasonic probe assembly in accordance with claim 11, wherein said first rotating means comprises a first stepper motor.

13. An ultrasonic probe assembly in accordance with claim 12, wherein said second rotating means comprises a second stepper motor.

14. The ultrasonic probe assembly in accordance with claim 11, further comprising a second flexible tubular connection means connected to said second housing on one end and having connector means disposed on the other end for connecting said second housing to said control means.

15. The ultrasonic probe in accordance with claim 11, wherein said control means includes pulse generating means for generating said first and second open loop electrical control signals as respective first and second pulse trains.

16. The ultrasonic probe in accordance with claim 15, wherein said pulse generating means includes microstepping pulse means for generating analog signals in combination with said first and second pulse trains.

17. The ultrasonic probe in accordance with claim 16, wherein said pulse generating means generates sinusoidal signals.

18. An ultrasonic probe apparatus, comprising:

a probe housing;

an ultrasonic transducer array disposed in said probe housing said transducer array including a gear;

first rotating means having an output shaft with a bevel gear engaging said gear of said ultrasonic transducer array for rotating said ultrasonic transducer array about a first axis through a predetermined angle, said first rotating means coupled to said control means to rotate said transducer array in response to said first open loop electrical control signal;

second rotating means connected to said ultrasonic transducer array for rotating said transducer array about a second axis through a predetermined angle, said second rotating means coupled to said control means to rotate said transducer array in response to said second open loop electrical signal, said second axis to perpendicular said first axis;

said first rotating means disposed within said probe housing;

said bevel gear and said transducer gear disposed within said probe housing; and control means operatively connected to said first and second rotating means for generating said first and second open loop electrical control signals.

19. The ultrasonic probe apparatus in accordance with claim 18, wherein said first rotating means comprises a first stepper motor.

20. The ultrasonic probe apparatus in accordance with claim 19, wherein said second rotating means comprises a second stepper motor.

21. The ultrasonic probe in accordance with claim 18, wherein said control means includes pulse generating means for generating said first and second open loop electrical control signals as respective first and second pulse trains.

22. The ultrasonic probe in accordance with claim 21, wherein said pulse generating means includes microstepping pulse means for generating analog signals in combination with said first and second pulse trains.

23. The ultrasonic probe in accordance with claim 22, wherein said pulse generating means generates sinusoidal signals.

24. An ultrasonic probe, comprising:

an ultrasonic transducer array;

control means for generating a first and second open loop electrical control signal;

first stepper motor connected to said ultrasonic transducer array for rotating said ultrasonic transducer array about a first axis through a predetermined angle in response to an open loop electrical control signal; and second stepper motor connected to said ultrasonic transducer array for rotating said transducer array about a second axis through a predetermined angle in response to a second electrical control signal, said second axis perpendicular to said first axis;

said control means including microstepping pulse means for generating analog signals in combination with pulse trains to provide sinusoidal signals as said first and second open loop electrical control signals.

25. The ultrasonic probe in accordance with claim 24, further comprising a probe housing, said transducer array and said first stepper motor disposed within said probe housing.

26. The ultrasonic probe in accordance with claim 25, wherein said first stepper motor is disposed within said probe housing.

27. The ultrasonic probe in accordance with claim 24, wherein said first stepper motor further comprises a semi-circular bevel gear, said transducer array is connected to said bevel gear, and said bevel gear is operatively connected to said first stepper motor, whereby the rotation of said first stepper motor through a predetermined angle causes said bevel gear and said transducer array to rotate about said first axis by a predetermined proportional amount.

28. The ultrasonic probe in accordance with claim 24, wherein said second stepper motor further comprises a pulley connected to said transducer array, said pulley operatively connected to said second stepper motor by a cable, said pulley having a depression on the rim and said cable having a bulb engaging said depression, whereby the rotation of said second stepper motor through a predetermined angle causes said pulley and said transducer array to rotate about said second axis by a predetermined proportional amount.

* * * * *